United States Patent
Shain

(10) Patent No.: US 8,093,020 B2
(45) Date of Patent: Jan. 10, 2012

(54) ALLELIC DISCRIMINATION ANALYSIS USING AN EFFICIENCY RELATED VALUE (EFR)

(75) Inventor: Eric B. Shain, Glencoe, IL (US)

(73) Assignee: Abbott Laboratories, Abbott Park, IL (US)

( * ) Notice: Subject to any disclaimer, the term of this patent is extended or adjusted under 35 U.S.C. 154(b) by 30 days.

(21) Appl. No.: 12/343,233

(22) Filed: Dec. 23, 2008

(65) Prior Publication Data

US 2009/0246777 A1    Oct. 1, 2009

Related U.S. Application Data

(60) Provisional application No. 61/060,742, filed on Jun. 11, 2008, provisional application No. 61/017,531, filed on Dec. 28, 2007.

(51) Int. Cl.
*C12P 19/34* (2006.01)
(52) U.S. Cl. ...................................................... 435/91.2
(58) Field of Classification Search ................... 435/91.2
See application file for complete search history.

(56) References Cited

U.S. PATENT DOCUMENTS

| | | | |
|---|---|---|---|
| 5,140,236 A | 8/1992 | Kawamura et al. | |
| 2003/0148302 A1* | 8/2003 | Woo et al. | 435/6 |
| 2005/0130211 A1 | 6/2005 | Shain | |
| 2007/0073490 A1 | 3/2007 | Kurnik et al. | |
| 2008/0299583 A1 | 12/2008 | Shain | |
| 2009/0047679 A1 | 2/2009 | Shain | |

FOREIGN PATENT DOCUMENTS

WO   WO 2009/086415   9/2009

OTHER PUBLICATIONS

Yuan et al. BMC Bioinformatics, vol. 7 (85), pp. 1-12, Feb. 2006.*

PCT International Search Report and Written Opinion dated Mar. 2, 2009 issued in PCT/US08/088220 (WO 2009/086415).
PCT International Preliminary Report on Patentability dated Jun. 29, 2010 issued in PCT/US08/088220 (WO 2009/086415).
*Applied Biosystems* (2006/2010) "Allelic Discrimination Getting Started Guide (PN 4347822E)", pp. 1-86.
Bernard et al. (2000) "Homogeneous amplification and variant detection by fluorescent hybridization probes." *Clin. Chem.*, 46(2):147-148.
Heid et al. (1996) "Real Time Quantitative PCR" *Genome Res.*, 6: 986-989.
Osgood-McWeeney et al. (2000) "Allelic Discrimination for Single Nucleotide Polymorphisms in the Human Scavenger Receptor Class B Type 1 Gene Locus Using Fluorescent Probes" *Clin. Chem.*, 46(1): 118-131.
Pfaffl (2004) "Quantification Strategies in real-time PCR" Chapter 3 in: *A-Z of quantitative PCR* , pp. 87-112.
Wong et al. (2005) "Real-time PCR for mRNA quantitation" *Biotechniques*, 39(1):1-11.

* cited by examiner

*Primary Examiner* — Gary Benzion
*Assistant Examiner* — Cynthia Wilder
(74) *Attorney, Agent, or Firm* — Emily M. Haliday; Weaver Austin Villeneuve & Sampson LLP

(57) ABSTRACT

In various embodiments this invention provides novel methods for discriminating two or more different target nucleic acids. In certain embodiments the methods comprise providing data amplification reactions comprising reagents to amplify two or more different target nucleic acids where the data comprise signals comprising an amplitude measurement representing the degree of amplification of each target nucleic acid in the amplification reaction and the time point in the amplification reaction at which the amplitude is measured; determining an efficiency related transform of the data, determining an efficiency related value for each target nucleic acid that is the maximum magnitude of the efficiency related transform; and outputting the efficiency related values in the amplification reaction for each target nucleic acid, where the relative amplitudes of the efficiency related values for each target nucleic acid is an indicator of the presence of each of said nucleic acids in said sample.

29 Claims, 14 Drawing Sheets

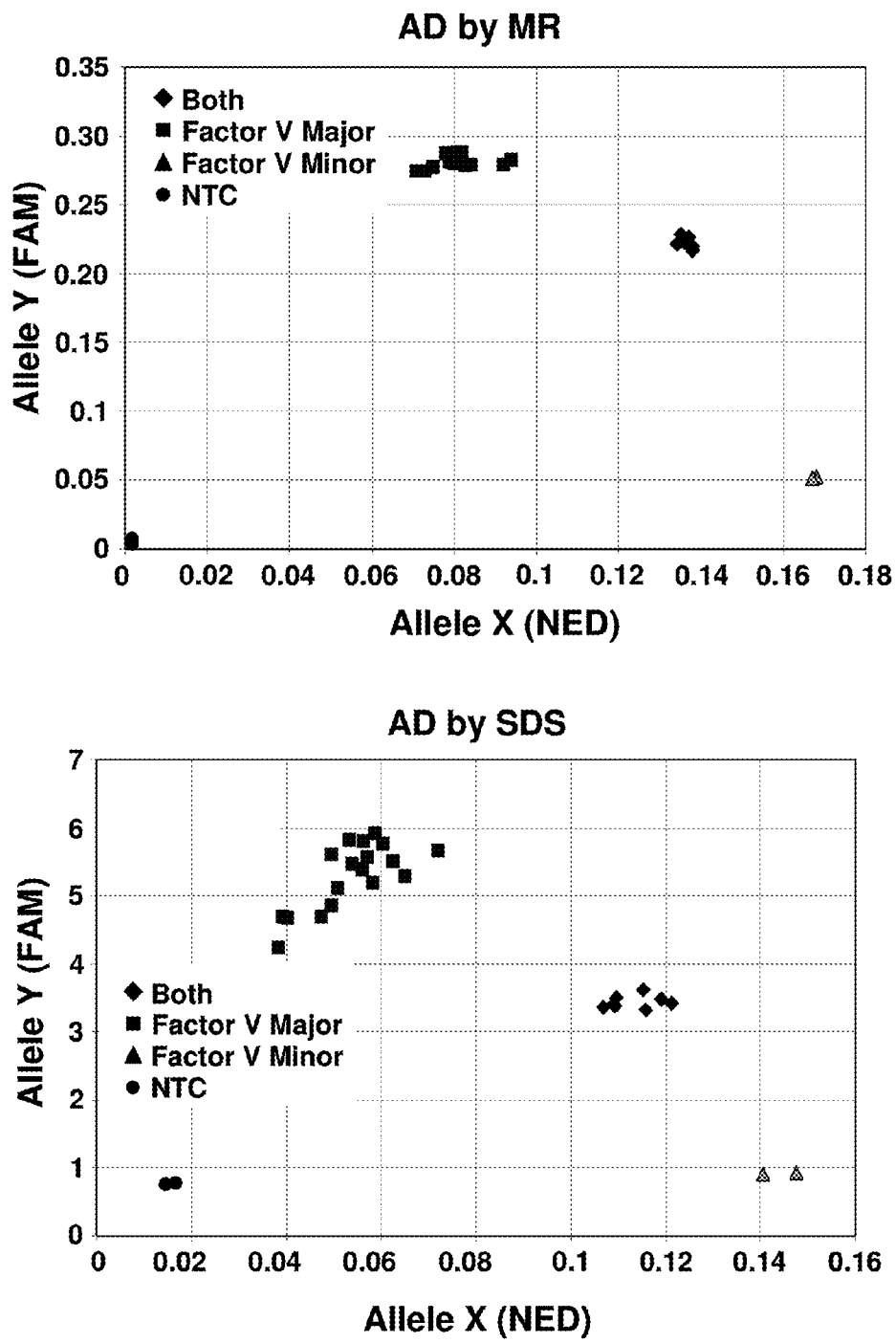
*Fig. 3, cont'd.*

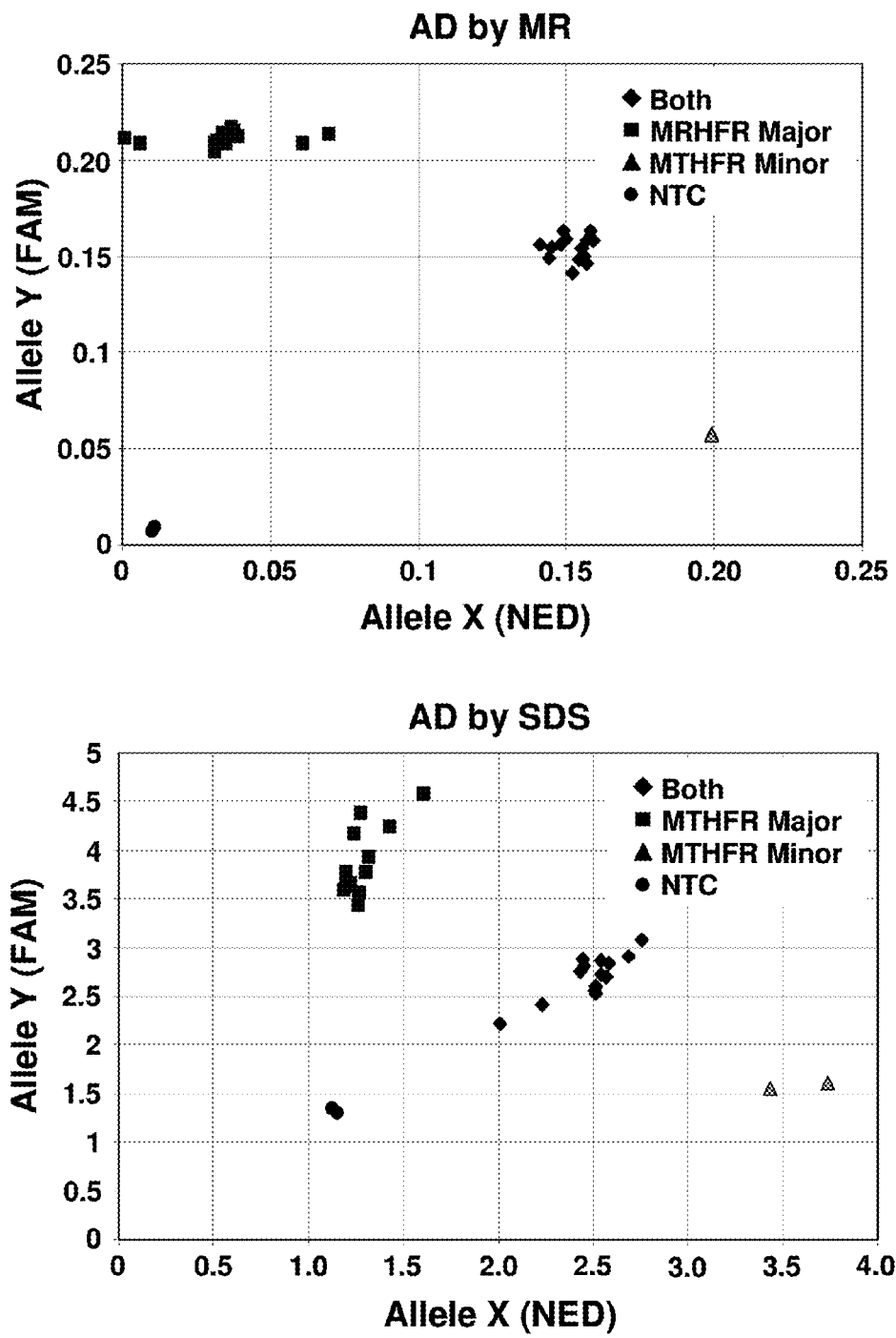
Fig. 3, cont'd.

ALLELIC DISCRIMINATION ANALYSIS USING AN EFFICIENCY RELATED VALUE (EFR)

CROSS-REFERENCE TO RELATED APPLICATIONS

This application claims priority to and benefit of U.S. Ser. No. 61/060,742, filed on Jun. 11, 2008 and U.S. Ser. No. 61/017,531, filed on Dec. 28, 2007, both of which are incorporated herein by reference in their entirety for all purposes.

COPYRIGHT NOTICE

Pursuant to 37 C.F.R.1.71(e), applicants note that this disclosure contains material that is subject to and for which is claimed copyright protection, such as, but not limited to, source code listings, screen shots, user interfaces, user instructions, and any other aspects of this submission for which copyright protection is or may be available in any jurisdiction. The copyright owner has no objection to the facsimile reproduction by anyone of the patent document or patent disclosure, as it appears in the records of the Patent and Trademark Office. All other rights are reserved, and all other reproduction, distribution, creation of derivative works based on the contents, public display, and public performance of the application or any part thereof are prohibited by applicable copyright law.

STATEMENT AS TO RIGHTS TO INVENTIONS MADE UNDER FEDERALLY SPONSORED RESEARCH AND DEVELOPMENT

Not Applicable

FIELD OF THE INVENTION

The present invention relates to analysis of data of nucleic acid amplification reactions. More specifically, in certain embodiments the invention relates to an information system and methods for making performing allelic discrimination and/or the detection/discrimination of other nucleic acids using real-time nucleic acid amplification including, but not limited to, PCR analysis.

BACKGROUND OF THE INVENTION

Nucleic acid sequence analysis is becoming increasingly important in many research, medical, and industrial fields (see, e.g., Caskey (1987) *Science* 236: 1223-1228; Landegren et al. (1988) *Science,* 242: 229-237; Arnheim et al. (1992) *Ann. Rev. Biochem.,* 61: 131-156, etc.). In particular, more than 2,000 conditions have been identified as single-gene defects for which the risk of producing affected offspring can be mathematically predicted. Among these conditions in man include Huntington's chorea, cystic fibrosis, $\alpha_1$ antitrypsin deficiency, muscular dystrophy, Hunter's syndrome, Lesch-Nyhan syndrome, Down's syndrome, Tay-Sachs disease, hemophilias, phenylketonuria, thalasemias, and sickle-cell anemia. In addition to various genetic diseases can be diagnosed utilizing nucleic acid sequence analysis, various infectious diseases can be diagnosed by the presence in a clinical sample of a specific DNA sequence characteristic of the causative microorganism. These include, but are not limited to bacteria, viruses, and parasites. In addition, particular pathogen strains (e.g., drug resistant pathogens) can be identified by nucleic acid analysis. Also the identification of various nucleic acid polymorphisms has utility for basic research, genotyping, and forensics.

Current diagnostic techniques for the detection of known nucleotide differences include: hybridization with allele-specific oligonucleotides (ASO) (Ikuta, et al., Nucleic Acids Research 15: 797-811 (1987); Nickerson, et al., PNAS (USA) 87: 8923-8927 (1990); Saiki, et al., PNAS (USA) 86: 6230-6234 (1989); Verlaan-de Vries, et al., Gene 50: 313-320 (1980); Wallace, et al., Nucleic Acids Research 9:879-894 (1981); Zhang, Nucleic Acids Research 19: 3929-3933 (1991)); allele-specific PCR (Gibbs, et al., Nucleic Acids Research 17: 2437-2448 (1989); Newton, et al., Nucleic Acids Research 17: 2503-2516 (1989)); solid-phase minisequencing (Syvanen, et al., American Journal of Human Genetics 1993; 52: 46-59 (1993)); oligonucleotide ligation assay (OLA) (Grossman, et al., Nucleic Acids Research 22: 4527-4534 (1994); Landegren, et al., Science 241: 1077-1080 (1988)); and allele-specific ligase chain reaction (LCR) (Abravaya, et al. (1995) *Nucleic Acids Res.* 23: 675-682; Barany, et al. (1991) *Proc. Natl. Acad. Sci., USA,* 88: 189-193; Wu, et al., (1989) *Genomics* 4: 560-569). Genomic DNA is analyzed with these methods by the amplification of a specific DNA segment followed by detection analysis to determine which allele is present.

The routine use of nucleic acid amplification reactions for allelic detection/discrimination, particularly in clinical settings, has been hampered because the quantification of nucleic acids is made more difficult or less accurate or both because data captured during amplification reactions are often significantly obscured by signals that are not generated in response to the target nucleic acid (i.e., noise). Furthermore, the data captured by many monitoring methods can be subject to variations and lack of reproducibility due to conditions that can change during a reaction or change between different instances of a reaction.

SUMMARY OF THE INVENTION

In certain embodiments this invention pertains to the discovery that the use of the maximum value of an efficiency related transform of amplification data provides an effective analytical tool for distinguishing different nucleic acid targets in such an amplification.

Accordingly in certain embodiments methods are provided for discriminating two or more different target nucleic acids. These methods typically involve providing data from one or more amplification reactions comprising reagents to amplify two or more different target nucleic acids from a single sample where the data comprise signals comprising an amplitude measurement representing the degree of amplification of each target nucleic acid in the amplification reaction and the time point in the amplification reaction at which the amplitude is measured where the signal provides such data for a multiplicity of time points in the amplification reaction(s); determining an efficiency related transform of the data where the efficiency related transform provides an amplitude measure that is related to the efficiency of amplification in the reaction; determining an efficiency related value for each target nucleic acid that is the maximum magnitude of the efficiency related transform determined for that target nucleic acid; and outputting to a display, printer, or storage medium the efficiency related values for each target nucleic acid, where the relative amplitudes of the efficiency related values for each target nucleic acid is an indicator of the presence of each of the nucleic acids in the sample. In certain embodiments the reagents to amplify two or more target nucleic acids are in a single amplification reaction. In certain embodiments the reagents to amplify two or more target nucleic acids distributed/segregated so that each amplification reaction comprises reagents to amplify different target nucleic acids. In certain embodiments reactions are run in one combined reaction mix and in other segregated reaction mixes. In certain embodiments the providing comprises reading a data file from a PCR reaction, or real-time monitoring of a PCR reaction, or receiving such values through a network connection. In various embodiments the time points in the amplification reaction are measured in cycle number or in reaction time. In certain embodiments the methods involve discriminating at least 3, or at least 4 or at least 5 or at least 6 different target nucleic acids. In certain embodiments the target nucleic acids comprise a first nucleic acid derived from a first allele of a gene and a second nucleic acid derived from a second allele of the gene. In certain embodiments the outputting comprises outputting information indicating whether the sample is homozygous for the first allele, homozygous for the second allele or heterozygous for both alleles. In various embodiments the efficiency related transform is selected from the group consisting of the ratio transform of the signals, the shifted ratio transform of the signals, the first derivative of the signals, the differences between sequential signals, and the slope or gradient of the log of the signals. In certain embodiments the efficiency related transform (ERT) is calculated as:

$$ERT = (Signal_{n+1}/Signal_n) - 1 \quad \text{or} \tag{a}$$

$$ERT = (Signal_n/Signal_{n-1}) - 1 \tag{b}$$

where $Signal_n$ is the signal produced at cycle number n, $Signal_{n+1}$ is the signal produced at the subsequent cycle number, $Signal_{n-1}$ is the signal produced at the previous cycle number, and n ranges from 1 up to the number of amplification cycles analyzed in the reaction for formula (a) and n ranges from 2 up to the number of amplification cycles−1 analyzed in the reaction for formula (b). In certain embodiments the efficiency related value is the maximum of the efficiency related transform, or the maximum gradient of the log of the amplification response, or the maximum ratio of the amplification response, or the maximum first derivative of the amplification response. In certain embodiments additional signal values are generated by interpolating points between the measured signal values (e.g., using cubic splines). In certain embodiments the efficiency related transform additionally provides a measure of the time or cycle number in the amplification reaction(s). In certain embodiments the method further comprises calculating a reaction point that is the fractional cycle number or time at which the maximum magnitude of the efficiency related transform occurs. In certain embodiments the method further comprises calculating an adjusted reaction point (e.g., an adjusted reaction point equal to the reaction point minus the log base 2 of the efficiency related value). In certain embodiments the adjusted reaction point is equal to the reaction point minus the log base 2 of the signal intensity above background. In certain embodiments the determining an efficiency related value for each target nucleic acid that is the maximum magnitude comprises identifying a peak in the efficiency related transform as a function of time or cycle number. The method can then further comprise determining the width of the peak; comparing the width of the peak to a selected range of acceptable peak widths; and outputting to a display, printer, or storage medium and indicator identifying the nucleic acid amplification reaction as possibly abnormal if the peak width determined is greater than or less than a selected range of acceptable peak widths. In certain embodiments the peak width is calculated using only efficiency related transforms that occur at or before the reaction point value of the efficiency related value. In various embodiments the amplification reaction is performed with a set of probes that comprises a FRET probe that is complementary to all or a portion of one of the amplified target nucleic acids. In certain embodiments the amplification reaction is performed with a set of probes that comprise a molecular beacon that is complementary to all or a portion of one of the amplified target nucleic acids. In certain embodiments the providing data comprises a modality selected from the group consisting of reading a data file containing the data, receiving the data from a network connection or feed, and receiving the data from an amplification reaction in realtime.

In various embodiments this invention also provides a machine-readable medium that provides instructions that, if executed by a machine, will cause the machine to perform operations comprising the analyses as described herein.

Also provided is a system comprising a device for performing a nucleic acid amplification and providing output signals that comprises a measure of the time point of the reaction, and the magnitude of the amplification of a target nucleic acid; a processor operably coupled to said device; and a machine-readable medium as described herein.

DEFINITIONS

The term "target nucleic acid" refers to a nucleic acid (often derived from a biological sample), that the amplification reaction is designed to amplify and or detect and/or quantify. It is either the presence or absence of the target nucleic acid that is to be detected, or the amount of the target nucleic acid that is to be quantified. In various embodiments, the term "target nucleic acid" refers to a nucleic acid all or a portion of which is to be amplified. Thus the target nucleic acid can comprise the template for an amplification reaction or a nucleic acid derived therefrom.

As used herein, the term "derived from a nucleic acid" refers to a nucleic acid nucleic acid for whose synthesis the referenced nucleic acid or a subsequence thereof has ultimately served as a template. Thus, for example, a DNA reverse transcribed or RT-PCR'd from an mRNA, an RNA transcribed from that cDNA, a DNA amplified from the cDNA, an RNA transcribed from the amplified DNA, etc., are all derived from the mRNA. A DNA amplified from a template comprising a gene, a DNA reverse transcribed from the transcript of that gene, a DNA amplified from the reverse transcript are all derived from that gene (nucleic acid).

DETAILED DESCRIPTION

Figure 1:
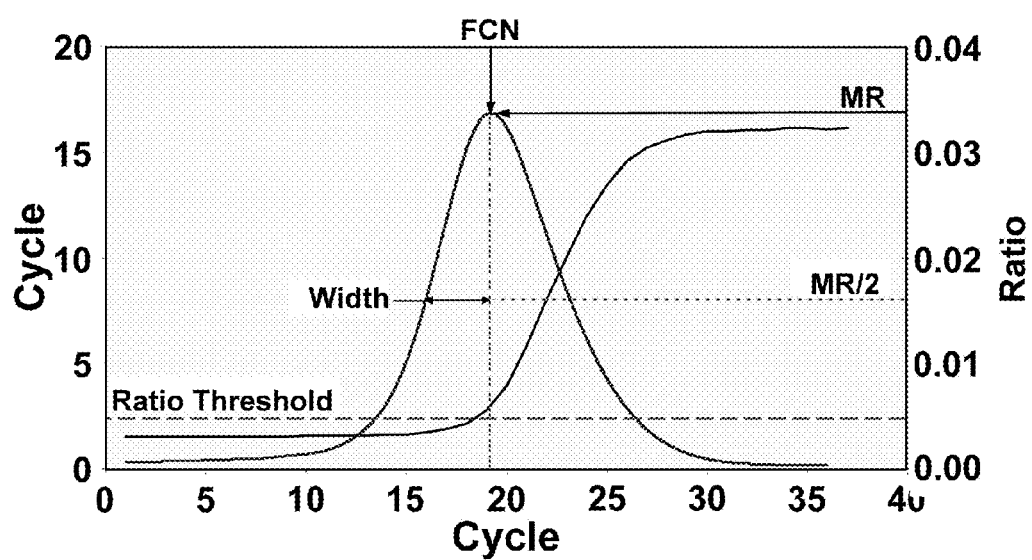
FIG. 1 illustrates a ratio transform showing MR, FCN and width definition.

This invention pertains to improved methods of detecting and discriminating closely related nucleic acid in a nucleic acid amplification reaction. The methods are easily implemented using conventional technology and are effectively detect and discriminate even single nucleotide differences thereby provide powerful methods for allelic discrimination, the detection of single nucleotide polymorphisms, and the like.

The method are applicable to the analysis of multiple target nucleic acids (e.g., different alleles of a gene) in a single amplification reaction. Typical allelic discrimination assays are multiplexed amplification assays comprising where at least two different target nucleic acids are amplified in the same reaction mixture. In various embodiments the multiplexed reaction mixture contain reagents to amplify at least 3, at least four, or at least 5 different target nucleic acids.

Conventional" allelic discrimination analysis is performed using an "end-point" assay system which attempts to determine the "amount" of amplification by measuring the amount of fluorescence (signal) generated for each target nucleic acid (e.g., allele) in the reaction, which should relate to whether that target nucleic acid is present. Total fluorescence generated in a PCR reaction, however, is not necessarily well related to efficiency of amplification. A higher concentration but less efficient amplification can generate more fluorescence than a higher efficiency but lower concentration amplification In addition, final fluorescence is generally determined after the PCR reaction has gone beyond the exponential amplification region where other aspects of the reaction can significantly affect performance. For this reason, final fluorescence levels are variable indicators of amplification. In addition in order to get adequate fluorescence measurements, a series of pre and post PCR fluorescence reads are required which increases the processing time.

More particularly, previous analysis methods primarily concentrate on quantitative responses that involve cycle number determination. These approaches provide a quantitative assessment by focusing on one portion of the amplification growth curve, namely the region of observed exponential growth. The cycle threshold or Ct-method (Heid et al. (1996) *Genome Res.*, 6: 986-989) determines a cycle number based on the point where the fluorescence response grows above the background level to cross a predetermined fluorescence threshold value. The critical steps involved in Ct determination include defining the baseline and establishing a suitable threshold for quantification of the target for use with either an external calibration curve or an internal quantitation standard. However, these methods are challenged when the growth curve signal exhibits anomalous features. In such cases, analysis often requires some measure of interpretation on the part of the data reviewer to assess whether a particular response is truly an amplification or not.

In contrast, the present invention utilizes an efficiency related transform (ERT) of amplification signals where the efficiency related transform provides a measure of the time or cycle number in the amplification reaction and an amplitude measure that is related to the efficiency of amplification in said reaction. It was a surprising discovery that the use of such efficiency related transforms in the analysis/discrimination of related nucleic acid targets provides improved sensitivity and discrimination of the targets.

In various embodiments the efficiency related transform involves the calculation of a ratio between sequential amplification measurements thereby yielding a series of ratios, each of which can be indexed to a time value or cycle number. In various embodiments amplification efficiency related values (MR values) are determined in the early cycles as the amplification rises above the background. Because these MR values are determined while the reaction is still near exponential, they are more directly related to amplification efficiency and provide better discrimination between target nucleic acids than conventional Ct analyses (see, e.g., FIGS. 2A, 2B, and 3) and are more useful for determining AD or SNP calls than total fluorescence. MaxRatio analysis uses most of the measurements from a real-time PCR reaction. For this reason, there is the ability to make measurements of the quality and validity of the PCR amplification not available in the total fluorescence method. In addition, using MR values only requires the PCR cycling protocol and eliminates the need the pre and post reads significantly reducing processing time.

I. Amplification Methods

The methods described herein are useful in discriminating related target nucleic acid sis any of a number of amplification methods.

Many systems have been developed that are capable of amplifying and detecting nucleic acids. Similarly, many systems employ signal amplification to allow the determination of quantities of nucleic acids that would otherwise be below the limits of detection. The present invention can utilize any of these systems, provided that a signal indicative of the presence of a nucleic acid or of the amplification of copies of the nucleic acid can be measured in a time-dependent or cycle-dependent manner. Some preferred nucleic acid detection systems that are useful in the context of the present invention include, but are not limited to, PCR, LCR, 3SR, NASBA, TMA, and SDA.

Polymerase Chain Reaction (PCR) is well-known in the art and is essentially described in Saiki et al. (1985) *Science* 230: 1350-1354; Saiki et al. (1988) *Science* 239: 487-491; and in U.S. Pat. Nos. 5,538,848; 5,723,591; and 5,876,930, and other references. PCR can also be used in conjunction with reverse transcriptase (RT) and/or certain multifunctional DNA polymerases to transform an RNA molecule into a DNA copy, thereby allowing the use of RNA molecules as substrates for PCR amplification by DNA polymerase (see, e.g., Myers et al. (1991) *Biochem.* 30: 7661-7666).

Ligation chain reactions (LCR) are similar to PCR with the major distinguishing feature that, in LCR, ligation instead of polymerization is used to amplify target sequences. LCR is described inter alia in European Patent 320 308; and by Landegren et al. (1988) *Science* 241(4869): 1077-1080; by Wu et al. (1989) *Genomics* 4(4): 560-569, and the like. In some advanced forms of LCR, specificity can be increased by providing a gap between the oligonucleotides, which gaps must be filled in by template-dependent polymerization. This can be especially advantageous if all four dNTPs are not needed to fill the gaps between the oligonucleotide probes and all four dNTPS are not supplied in the amplification reagents. Similarly, rolling circle amplification (RCA) is described by Lisby (19999) *Mol. Biotechnol* 12(1): 75-99), Hatch et al. (19999) *Genet. Anal.* 15(2): 35-40, and others, and is useful in the context of the present invention.

Isothermal amplification reactions are also known in the art and useful in the context of the present invention. Examples of isothermal amplification reactions include 3SR as described by Kwoh et al. (1989) *Proc. Natl. Acad. Sci., USA*, 86: 1173-1177 and further developed in the art; NASBA as described by Kievits et al. (1991) *J. Virol. Meth.* 35: 273-286, and further developed in the art; and Strand Displacement Amplification (SDA) method as initially described by Walker et al. (1992) *Proc. Natl. Acad. Sci., USA,* 89: 392-396 and U.S. Pat. No. 5,270,184, and further developed in the art.

Thus, many amplification or detection systems requiring only that signal gains indicative of the quantity of a target nucleic acid can be measured in a time-dependent or cycle-dependent manner are useful in the context of the present invention. Other systems having these characteristics are known to the skilled artisan, and even though not discussed above, are useful in the context of the present invention.

For clarity, the invention will be illustrated with reference to real-time PCR reactions, however, it will be recognized that the methods are equally applicable to other amplification systems including, but not limited to the other amplification systems describe herein.

Real-time PCR combines amplification of nucleic acid (NA) sequence targets with substantially simultaneous detection of the amplification product. Optionally, detection can be based on fluorescent probes or primers that are quenched or are activated depending on the presence of a target nucleic acid. The intensity of the fluorescence is dependent on the concentration or amount of the target sequence in a sample (assuming, of course, that the quantity of the target is above a minimal detectable limit and is less than any saturation limit). This quench/fluoresce capability of the probe allows for homogeneous assay conditions, i.e., all the reagents for both amplification and detection are added together in a reaction container, e.g., a single well in a multi-well reaction plate. Electronic detection systems, target-capture based systems, and aliquot-analysis systems and techniques are other forms of detection systems useful in the context of the present invention so long as a given system accumulates data indicative of the quantity of target present in a sample during various time points of a target amplification reaction.

In allelic discrimination systems, the amplification is multiplexed. That is, each reaction typically comprises primers that specifically amplify at least two different target nucleic acids. In addition, the systems typically include probes for the detection of the amplification products.

In PCR reactions, the quantity of target nucleic acid doubles at each cycle until reagents become limiting or are exhausted, there is significant competition, an inadequate supply of reactants, or other factors that accumulate over the course of a reaction. At times during which a PCR reaction causes doubling (exactly) of the target in a particular cycle, the reaction is said to have an efficiency (e) of 1 (e.g., e=1). After numerous cycles, detectable quantities of the target can be created from very small and initially undetectable quantity of target. Typically, PCR cycling protocols consist of between around 30-50 cycles of amplification, but PCR reactions employing more or fewer cycles are known in the art and useful in the context of the present invention.

In the real-time PCR reactions described below to illustrate the present invention, the reaction mixture includes an appropriate reagent cocktail of oligonucleotide primers, fluorescent dye-labeled oligonucleotide probes capable of being quenched (or de-quenched) when not bound to a complementary target nucleic acid, or intercalating dyes, amplification enzymes, deoxynucleotide triphosphates (dNTPs), and additional support reagents. Also, a second fluorescent dye-labeled oligonucleotide probe for detection of an amplifiable "control sequence" or "internal control" and a "reference dye", which optionally may be attached to an oligonucleotide that remains unamplified throughout a reaction series, can optionally be added to the mixture for a real-time PCR reaction. Thus, some real-time PCR systems use a minimum of three fluorescent dyes in each sample or reaction container (e.g., a well).

In various amplification systems, particularly where multiple target nucleic acids are amplified (e.g., in allelic discrimination), it is often desirable to multiplex amplification reactions. Thus a single amplification reaction can include primers to amplify and probes to detect two or more, in certain embodiments, three ro more, four or more, five or more different target nucleic acids. In such systems probes and/or labels are selected to provide a different an distinguishable signal for the amplification produce of each target nucleic acid.

While allelic discrimination reactions (e.g., reactions to determine the presence of two or more closely related nucleic acids) are often performed in multiplexed amplification reactions such multiplexing is not required. Thus for example different target nucleic acids can be detected in different reaction mixes (e.g., in different wells on a PCR plate). Also combinations of multiplexed and individual target amplification reactions can be utilized. Thus for example, three alleles can be detected using one reaction mix for all three targets, using a different reaction mix for each target nucleic acid, or using one reaction for two target nucleic acids and a second amplification reaction for the third target nucleic acid. In the various multi-reaction analyses, it is desirable that the target nucleic acids be derived from the same sample.

Systems that plot and display data for each of one, or possibly more, reactions (e.g., each well in a multi-well plate) are also useful in the context of the present inventions. These systems optionally calculate values representing the fluorescence intensity of the probe as a function of time or cycle number ($C_N$) or both as a two-dimensional plot (y versus x). Thus, the plotted fluorescence intensity can optionally represent a calculation from multiple dyes (e.g., different probe dyes, and/or optional control dyes and/or optional reference dyes) and can include subtraction of a calculated background signal. In PCR systems, such a plot is generally referred to as a PCR amplification curve and the data plotted can be referred to as the PCR amplification data.

In PCR, data analysis can be made difficult by a number of factors. Accordingly, various steps can be performed to account for these factors. For example, captured light signals can be analyzed to account for imprecision in the light detection itself. Such imprecision can be caused by errors or difficulties in resolving the fluorescence of an individual dye among a plurality of dyes in mixture of dyes (described below as "bleedover"). Similarly, some amount of signal can be present (e.g., "background signal") and can increase even when no target is present (e.g., "baseline drift"). Thus, a number of techniques for removing the background signal, preferably including the baseline drift, trend analysis, and normalization are described herein and/or are known in the art. These techniques are useful but are not required in the context of the present invention. (Baseline drift or trending can be caused by many sources, such as, for example, dye instability, lamp instability, temperature fluctuations, optical alignment, sensor stability, or combinations of the foregoing. Because of these factors and other noise factors, automated methods of identifying and correcting the baseline region are prone to errors).

As used herein, nucleic acid amplification reaction can refer both to amplification of a portion of the sequence of a target nucleic acid and to amplification and accumulation of a signal indicative of the presence of a target nucleic acid, with the former often being preferred to the latter.

II. Analytic Methods

The real time PCR (or other amplification) curve is a fluorescence response with a roughly sigmoidal shape that correlates to the growth of amplified product during the PCR amplification process. The shape of the PCR amplification curve reflects the dynamics of the PCR reaction for an individual sample which is uniquely controlled by the assay design which includes reactive components (primer and probe designs and concentrations, concentrations for enzymes, activators, buffers, dNTPs, etc.) and cycling conditions for the reaction. Traditional real time PCR data reduction methods utilize the Ct method. The Ct method utilizes a threshold, which is chosen to be fairly close to the baseline signal level that corresponds to the exponential growth region of the PCR curve. The interpolated cycle at which the signal rises above the threshold is the Ct value for the curve. The Ct method is an excellent method for providing quantitative PCR analysis because of the consistency in signal intensity during the exponential growth phase of the PCR. However, it is susceptible to error when challenged with signal anomalies such as spectral crosstalk or discontinuities due to bubbles or noise. In order to detect in the exponential growth region of the PCR curve, a low threshold is required. With a low threshold, it is difficult to discriminate between a false threshold crossing due to an anomalous signal, e.g., spectral crosstalk, which results in a Ct error and a true signal Ct value. Even small errors in the baselining process can cause even negative reactions to cross the threshold or for reactive signals to cross early or late.

Accordingly in various embodiments, the methods of this invention utilize a MaxRatio method that involves the ratio between sequential measurement in the amplification reaction. In this method, the ratio between sequential measurements is calculated, thereby yielding a series of ratios, each of which can be indexed to a time value or cycle number. Many suitable means of calculating these ratios exist, and any suitable means can be used. The simplest way of performing this ratio calculation utilizes the following function:

$$\text{Ratio}(n) = \frac{s(n+1)}{s(n)} \qquad \text{I}$$

where n represents the cycle number and s(n) represents the signal at cycle n. This calculation provides a curve that starts at approximately 1 in the baseline region of the response, increases to a maximum during the growth region, and returns to approximately 1 in the plateau region. A MATLAB expression that performs this calculation efficiently is the following:

Ratio=$s$(2:end,:)./$s$(1:end−1,:), where "s" represents the signal response matrix, with each column representing a separate response.

Figure 4:
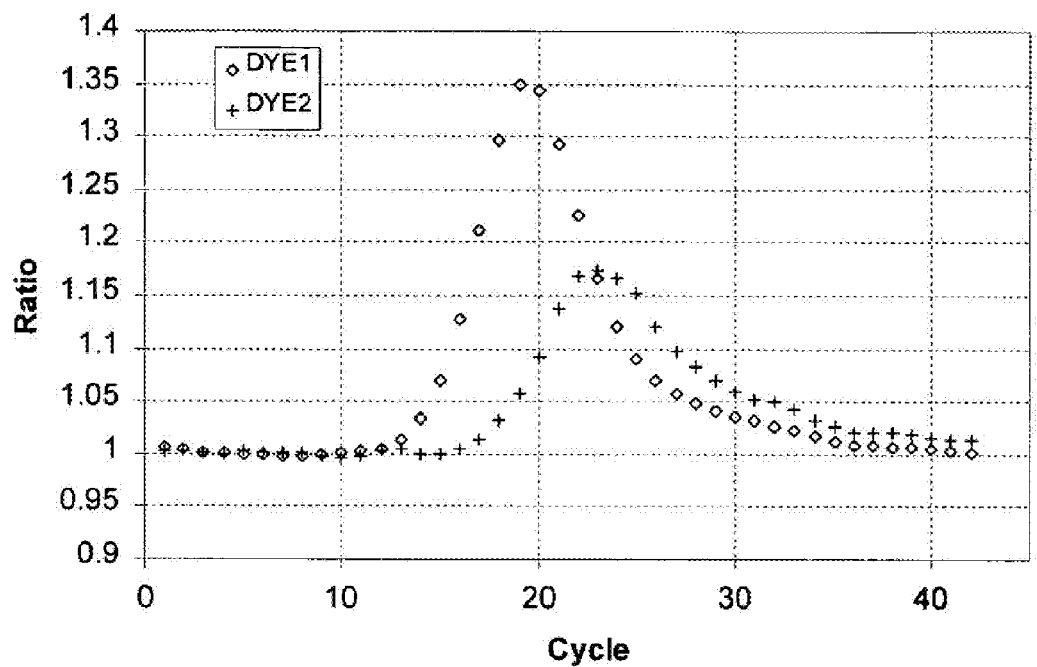
FIG. 4 shows a plot illustrating ratio transform of reaction target and control data according to embodiments of this invention.

FIG. 4 shows an example of this ratio transform. Because of the intrinsic background fluorescence, the ratio does not reach 2 as would be expected of a PCR reaction if the signal were doubling. Regardless, the magnitude of the peak is independent of multiplicative intensity variations and is proportional to the rate of growth or efficiency at that point. The method of calculating ratios is simple and efficiently calculated. Other equivalent calculations could be made. An example would involve calculating the forward and reverse ratios and then averaging them. On can use the inverse of the ratio, in which case the curve will begin at a value of approximately 1 in the baseline region, decrease in the growth region, and return to a value of approximately 1 in the plateau region. One would then use the magnitude and location of the trough instead of a peak for analysis. This transform can be implemented in a manner essentially equivalent to the ratio method.

Although the MaxRatio algorithm is usable as described, it is convenient to shift the curve by subtracting a constant, e.g., about one (1), from each point. This operation provides a transformation of the original response, which starts near zero in the baseline region, rises to a peak in the growth region of the curve, and returns near zero in the plateau region (see, e.g., FIG. 1). This shifted ratio calculation is described by the following function:

$$\text{Ratio}_n = \frac{\text{Signal}_n}{\text{Signal}_{n-1}} - 1 \qquad \text{II}$$

where $\text{Signal}_n$ is the measured real-time PCR fluorescence response for the target of interest at cycle n. The ratio calculation transforms the roughly sigmoidal shaped amplification curve to a ratio curve with a well-defined peak. FIG. 1 illustrates this transformation. The ratio curve exhibits several well-defined features.

The maximum value of the ratio curve defines two values. The cycle number at which the maximum occurs is defined as the FCN value or fractional cycle number. The magnitude of the ratio curve at the maximum is defined as the MR (maxRatio) value. The ratio curve has a characteristic width, measured as the half width at half maximum, referred to as the width parameter.

The ratio curve is a relative measure of the fluorescence signal growth throughout the PCR reaction. The early cycle ratio curve near zero represents the baseline region of the PCR curve and the late cycle region corresponds to the plateau phase. The ascending part of the ratio curve corresponds to the exponential growth phase; the descending part of the ratio curve is the transition from the exponential to the plateau phase in the PCR curve. The ratio equation is similar to the equation for the PCR reaction efficiency (Peirson et al. (2003) *Nucleic Acids Res.*, 31(14 e73)) at cycle n.

$$Efficiency_n = \frac{\Delta R_n}{\Delta R_{n-1}} - 1 \qquad \text{III}$$

Where $\Delta R_n$ is the baselined PCR signal intensity at cycle n. In practice, applying equation III to real amplification responses is problematic. Because the baselined PCR signal is approximately zero in the baseline portion of the curve, equation III suffers from division by zero problems. In addition, even trivial background slope variations cause significant changes in efficiency measurement in the exponential region. The signal value, $Signal_n$, in the ratio equation II includes the PCR signal intensity and the inherent background fluorescence level. As such, MR values are a relative measure of reaction efficiency. The magnitude of the MR value even for a perfectly efficient reaction is always less than one because of the inherent level of background fluorescence incorporated in the ratio equation. By including the background fluorescence in the ratio equation, the resulting ratio curve avoids division by zero problems and is highly insensitive to even moderate baseline slope variation.

Figure 5:
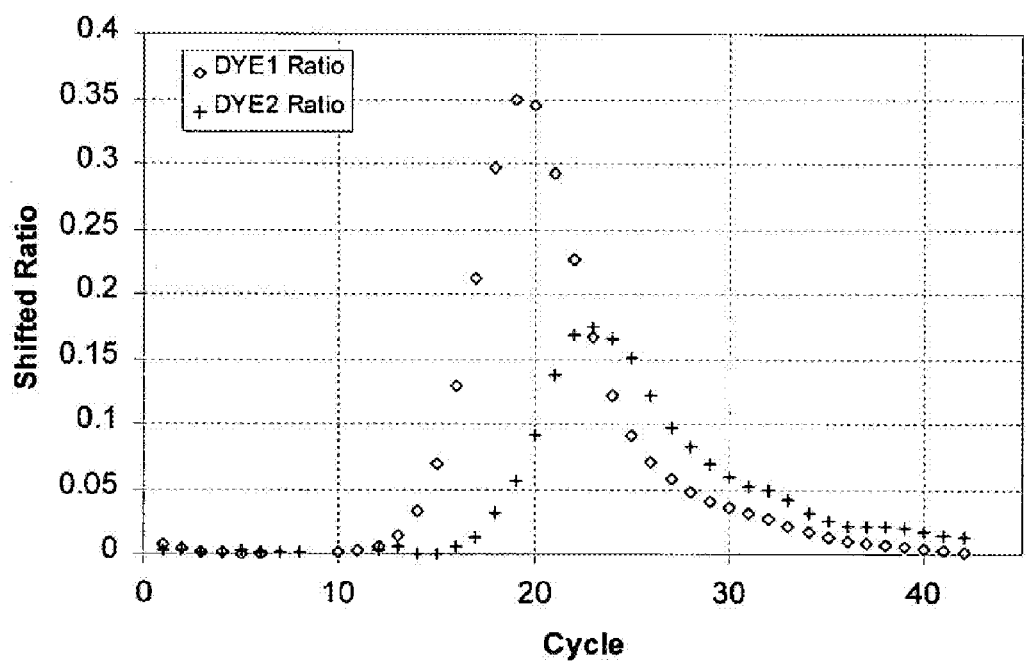
FIG. 5 is a plot illustrating shifted ratio transform of reaction target and control data according to embodiments of this invention.

FIG. 1 illustrates this the relationship of this calculation to simple Ct analysis, while FIG. 5 shows real output of this shifted ratio calculation. The reaction point and magnitude of the peak of the shifted ratio curve is then determined. The reaction point (i.e., distance along the x-axis) specifies the FCN value of the MR and the magnitude specifies the efficiency related value MR (Maximum of the Ratio).

Figure 6:
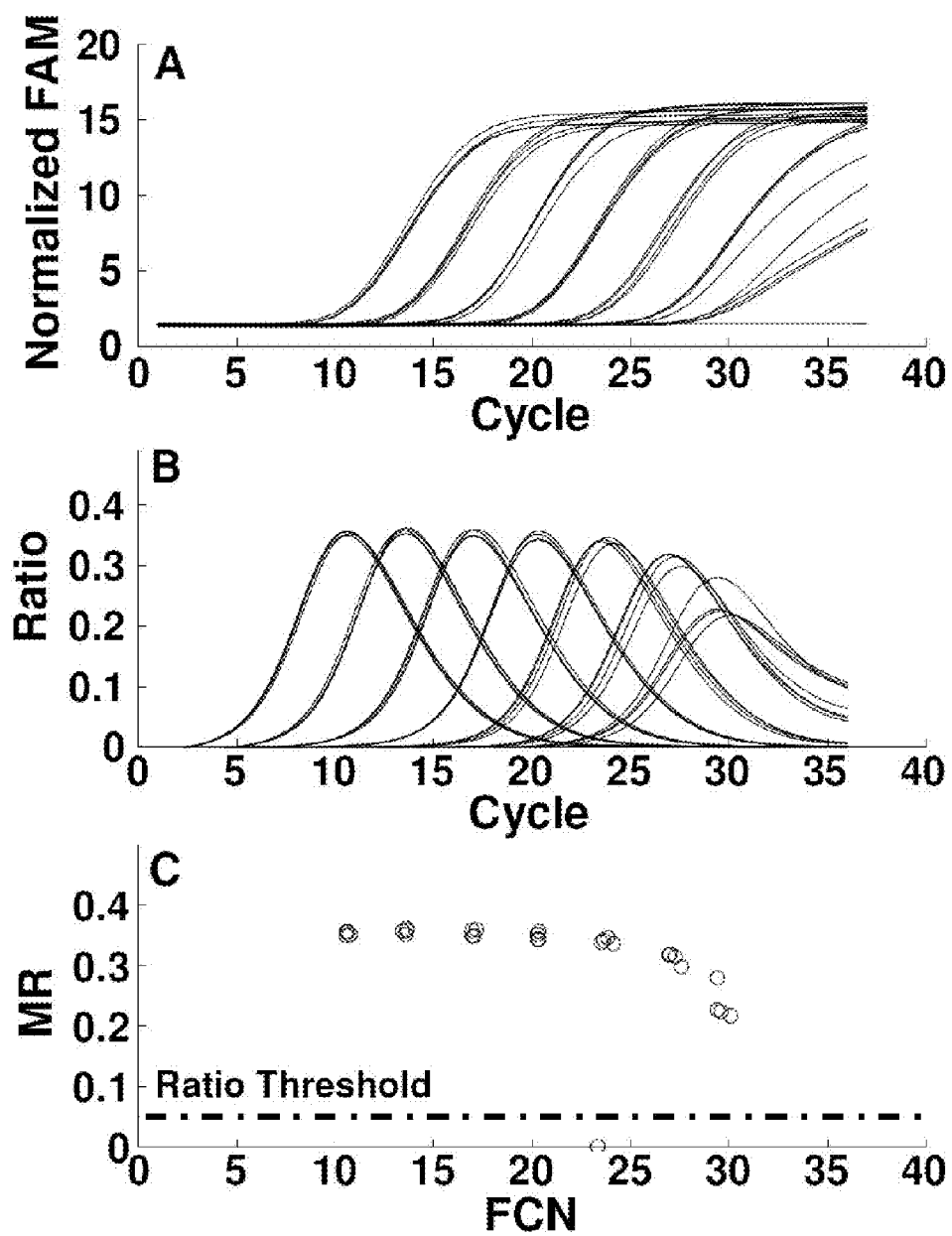
FIG. 6 shows the analysis by maxRatio of RealTime HIV-1 assay amplification plots. HIV-1 RNA ranging from 7.44 log 10 copies/mL to 1.56 log 10 copies/mL were tested in replicates of four using the m2000 sp and m2000rt instruments. (A) Amplification plots of the HIV-1 normalized FAM fluorescence versus cycle number. (B) Corresponding plots after applying the ratio transformation. (C) Plot of MR versus FCN values derived from the peaks of the ratio responses.

FIG. 6 illustrates an example dilution series of Abbott RealTime™ HIV-1 normalized FAM fluorescence processed with the maxRatio algorithm. Plotting the MR versus FCN values generates the characteristic MR-FCN plot for this data.

FIG. 6 represents amplification plots for a run of reactive samples. The only negative response is from the negative control, which is identified in the MR versus FCN plot with an MR value near zero. Since there is no signal growth in reactions without target, the ratio curve is nearly equal to zero throughout the amplification process. The MR value of approximately zero easily distinguishes the negative response from all the reactive samples. In practice a line can easily be established to separate these two populations of responses. This line is called the Ratio Threshold.

It will be appreciated that there are equivalent ratio calculations that provide a similar or essentially identical result. For example, a ratio calculation essentially equivalent to Formula II is:

$$Ratio_n = \frac{Signal_{n+1}}{Signal_n} - 1$$

This is meant to be illustrative and not limiting. Using the teachings provided herein, other efficiency related transforms, in particular ratio calculations will be available to one of skill in the art.

In one illustrative, but not limiting embodiment, the maxRatio method is implemented as part of the Abbott m2000 system. Because the m2000 system has an effective automatic baselining algorithm, baseline slope correction (but not offset) is applied. Although normalization and baseline slope correction are not required by the maxRatio method, a small but significant improvement in performance is achieved using them. In addition, the signal has a smoothing filter applied. It is a feature of the maxRatio method that a much more aggressive noise filter can be applied without significantly affecting the cycle number compared to the Ct method. The m2000rt instrument implements a fourth order, zero-phase noise filter. In order to obtain 0.01 cycle resolution, a cubic spline interpolation can be applied to the ratio curve.

It has been found that for assay responses with suppressed signal levels, the FCN value can shift slightly early. In order to provide more linear results, the adjusted FCN (FCNA) value can, optionally, be calculated using formula IV.

$$FCNA = FCN - \text{Log}_2(MR) \qquad \text{IV}$$

Because the ratio transformation is inherently self-compensating for reaction signal intensity, it can be applied to a reaction's raw fluorescence signal. When a reference dye is available, the normalized fluorescence signal can be analyzed. It should be noted that the fluorescence signal naturally has a background level of unquenched fluorescence. Because of the division in the ratio transformation, it is necessary to maintain this background fluorescence level to avoid division by zero. As an alternative to utilizing the raw or normalized fluorescence response directly, the response may be shifted to fixed positive background fluorescence level. The advantage of this response shifting is to eliminate sensitivity to factors that can change the level of background fluorescence such as variability in probe manufacture or fluorescence contamination in the thermal cycler block. The disadvantage to shifting the response is that it removes the inherent insensitivity to signal intensity and can introduce some instrument-to-instrument variability. For this reason, if shifting is implemented, using a shift value near the natural level of background fluorescence is recommended. It should be noted that shifting will directly affect the magnitude of the MR value. Shifting to a low value will increase both the MR value of positive reactions as well as the mean and standard deviation of the MR for negative reactions. In terms of statistical separation of populations, this rarely makes significant difference. However shifting to a low level can reduce robustness to spectral crosstalk, initial signal transients and other anomalies in the baseline portion of the amplification response. It is important therefore when developing the assay, to focus on separation of reactive from non-reactive populations by MR, not on maximizing the MR value.

III. Discriminating Alleles or Other "Related" Nucleic Acids

As indicated above, the above-described analytic methods are particular valuable in detecting/discriminating related nucleic acids (e.g., different alleles of a gene, strain variants of a pathogen, single nucleotide polymorphisms, and the like). In such assays, a nucleic acid sample is derived (obtained) from a biological sample. The term "biological sample" refers to sample that comprises a biological tissue, cell, fluid, pathogen, and the like that contains a nucleic acid that is to be detected/screened according to the assays described herein. Such samples include, but are not limited to, cultured cells, primary cell preparations, sputum, amniotic fluid, blood, tissue or fine needle biopsy samples, urine, peritoneal fluid, and pleural fluid, or cells therefrom. Biological samples can also include samples of pathogens (e.g., bacteria, viruses, parasites, etc.) that are either in primary samples (e.g., taken from an organism) or in samples that have been cultures. Biological samples may also include sections of tissues (e.g., frozen sections taken for histological purposes), and the like. The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

In various embodiments, the sample used for amplification can comprise genomic DNA and/or a nucleic acid derived from such. Thus, for example in certain embodiments, the sample can comprise an RNA, a DNA reverse transcribed from the RNA, and the like.

Amplification reactions are run according to standard methods well known to those of skill in the art. Typically the amplification reactions will be run with reagents (e.g., primers and probes) to specifically detect the target nucleic acids of interest. Thus, for example, where it is desired to detect different alleles (SNPs, etc.) primers and probes will be selected to amplify and detect all or part of the target nucleic acid. Where only a fragment of the target nucleic acid is to be detected, probes and primers are selected to amplify and detect that fragment of the nucleic acid that is expected to differ between the alleles.

The assays can be "multiplexed", or segregated, or both. In a multiplexed assay, a single amplification reaction (reaction mix) will contain primers and probes to amplify and detect at least two (in certain embodiments, at least 3, at least 4, at least 5, at least 6, etc.) different target nucleic acids. In segregated assays, a separate amplification reaction (reaction mix) will be used to amplify and detect each different target nucleic acid. In certain embodiments certain amplification reaction(s) (reaction mixes) can be used to each amplify and detect a single target nucleic acid while simultaneously other amplification reaction(s) (reaction mixes) each contain primers and probes to amplify and detect at least two different target nucleic acids. In "segregated" and "combined" assays it is desirable that the different amplification reactions are performed on a nucleic acid derived from the same sample.

Amplification data from the amplification reaction(s) can be acquired (e.g., using a computer system) and analyzed (e.g., as described above) to provide a measure of the presence and/or quantity of each target nucleic acids. In allelic discrimination analysis it is sometimes desirable to provide the analyzed information as a scatter plot showing the amplified values of each target nucleic acid (see, e.g., FIG. 2). In certain embodiments, the resulting data can be statistically analyzed (e.g., using cluster analysis, discriminant function analysis, and the like) to optimize the separation and detection of each target nucleic acid.

IV. Captured/Received Data

Figure 7:
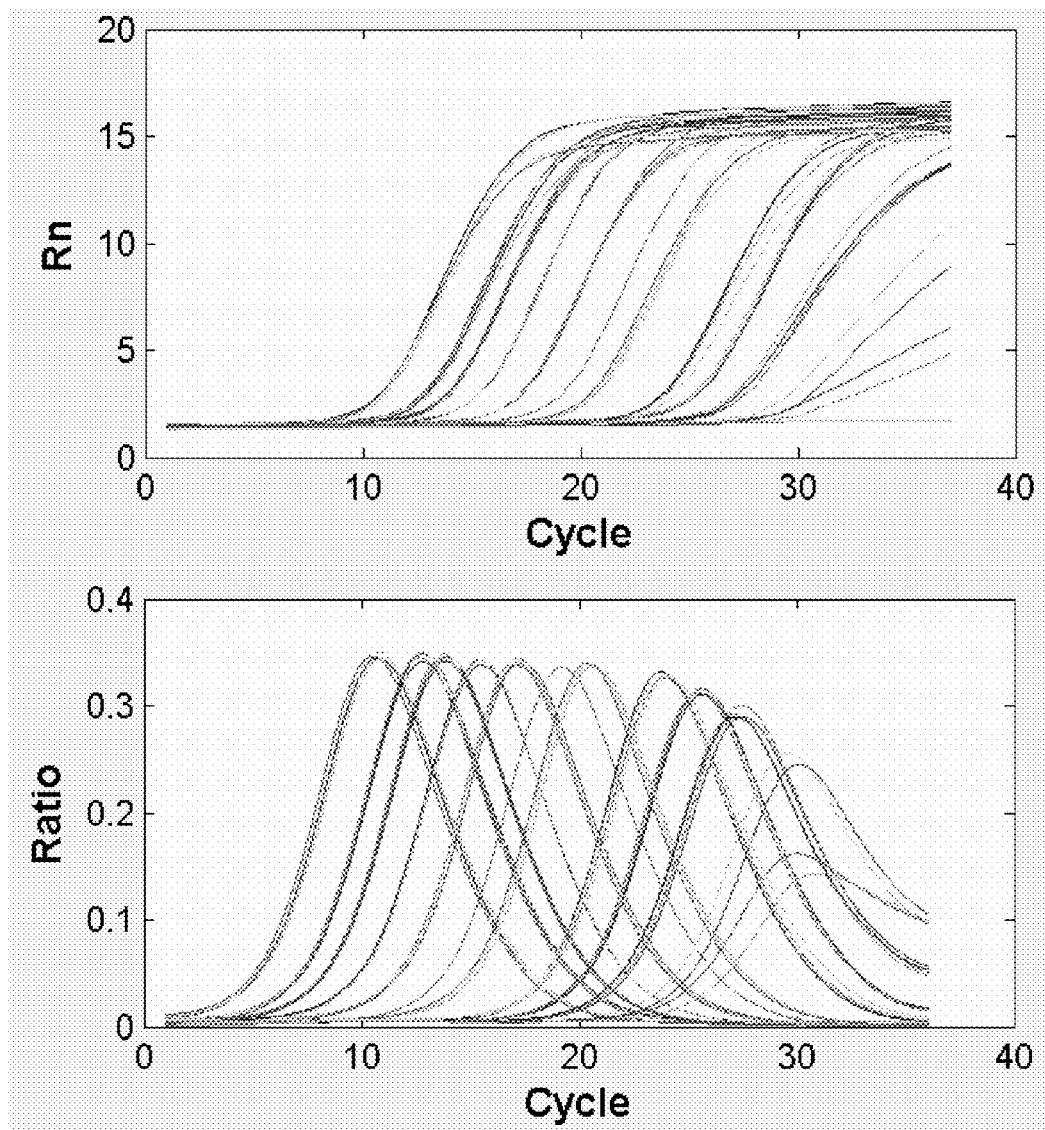
FIG. 7 shows reaction data for a number of target nucleic acids plotted as a function of cycle number (top panel) and ratio transforms of these data (bottom panel).

By way of example, a typical real-time PCR reaction detection system generates a data file that stores the signal generated from one or more detection dyes. These dyes can represent, for example, amplification data for two or more different target nucleic acids, and optionally, internal control data, and optionally reference data. FIG. 7, top panel, illustrates a plot of received/captured reaction data for a plurality of target nucleic acids that can be used in an analytical method according to the present invention. In this plot, the x-axis provides an indication of cycle number (e.g., 1 to 40) and the y-axis indicates dye intensity detected, in relative fluorescence units. In this figure, the different data sets are illustrated as continuous curves. However, the actual captured data values are generally discrete signal values captured at each cycle number.

As shown in FIG. 7, bottom panel, the data can be transformed (e.g., as described herein) using a ratio transformation which can provide a maximum ratio value, and optionally, a point at which the maximum ratio occurs, and optionally a peak width (e.g., full width at half max).

V. Optional Error Correction a) Normalization

Although optional, normalization can be performed on the captured data in several different ways. One method involves dividing the target and control values at each cycle reading by the corresponding reference dye signal. Alternatively, the divisor can be the average reference value over all cycles or an average over certain cycles. In another alternative embodiment, the divisor can be the average of the target dye or the control dye or the target dye and the control dye over one or more earlier (baseline) cycles, when no amplification signal is detected. Any known normalization method can be employed in a data analysis. The invention can be used with data that has already been normalized by a PCR system.

Because normalization is optional, the present invention can be used to analyze reaction data without the use of a normalization or reference dye. Alternatively, the target signal or the control signal or both can be used for normalization.

b) Scaling

Scaling is optional but can be performed to make it easier for a human operator to visualize the data. Scaling does not affect analytical results. Scaling can be carried out in addition to normalization, in the absence of normalization, or before or after normalization.

Figure 8:
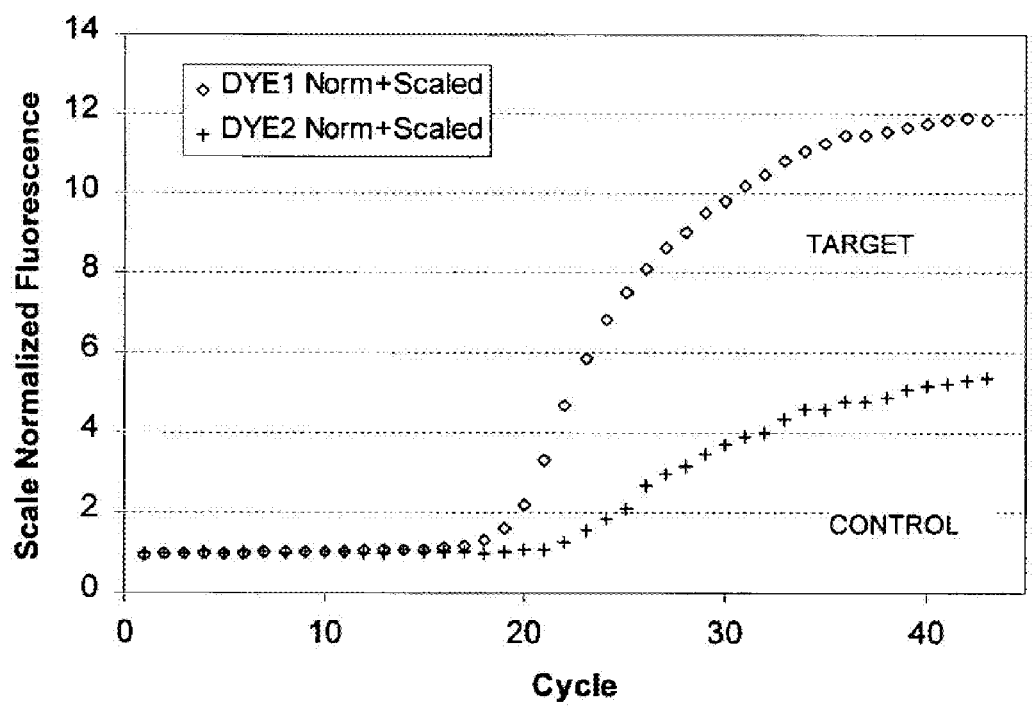
FIG. 8 from parent is a plot illustrating reaction data showing target and control data that have been scaled according to certain embodiments of this invention.

One method of scaling involves dividing each data set value by the average of the values during some early cycles, generally in the baseline region before any positive data signal is detected. In this example, readings 4 through 8 were averaged and normalization was performed first. FIG. 8 is a plot of reaction data showing target and control data that have been scaled. In this example, scaling forces the early values of the target and control to one, and because the early values are less than one, the division forces the later values to slightly larger pure numbers.

c) Digital Filtering

One or more digital filtering methods can be applied to the captured data to "clean up" the signal data sets and to improve the signal to noise ratio. Many different filtering algorithms are known. The present invention can employ a four-pole filter with no zeros. This eliminates the potential for overshoot of the filtered signal. As an example, this can be implemented with the MATLAB function "filtfilt" provided with the MATLAB Signal Processing Toolbox, which both forward and backward filters to eliminate any phase lag (time delays). An example of parameters and MATLAB function call is as follows:

```
b=0.3164;
a=[1.0000 -1.0000 0.3750 -0.0625 0.0039];
data(:,:,assay)=filtfilt(b,a,data(:,:,assay));
data(:,:,ic)=filtfilt(b,a,data(:,:,ic));
```

In this example, "b" and "a" contain the filter coefficients. "data(:,:,assay)" and "data(:,:,ic)" contain the captured data that may or may not have been normalized, scaled, or both. In this case, the filtered data is both normalized and scaled.

d) Slope Removal/Baselining

An optional slope removal method can be used to remove any residual slope that is present in the early baseline signal before any detectable actual signal is produced. This procedure may also be referred to as baselining, but in some embodiments, the offset is not removed, only the slope. In certain embodiments, for slope removal, both the target (DYE1) and, when present, control (DYE2) signals are examined simultaneously. Whichever signal (when present) comes up first defines the forward regression point, and the method generally goes back 10 cycles. If 10 cycles back is before cycle 5, then cycle 5 is used as the initial regression point to avoid any earlier signal transients. A linear regression line can be calculated using the signal data between these points and the slope of the regression for each dye is subtracted from that dye's signal. In this case, the slope removal is applied to the normalized, scaled, and filtered data discussed above.

VI. Systems, Devices, and Software

The methods of this invention can be incorporated into a multiplicity of suitable systems, computer products, and/or information instruments. Some details of a MR software implementation are provided below. Specific user interface descriptions and illustrations are taken to illustrate specific embodiments only and any number of different user interface methods known in the information processing art can be used in systems embodying this invention. The invention can also be used in systems where virtually all of the options described below are preset, calculated, or provided by an information system, and, consequently, provide little or no user interface options. In some cases, details and/or options of a prototype system are described for illustrative purposes; many of these options and/or details may not be relevant or available for a production system.

Furthermore, software embodiments can include various functionalities, such as, for example, processing reactions with two, three, four, or five or more target reactions, and, optionally, or one or more internal control reactions, or reference data, or combinations of the foregoing. A software system suitable for use in this invention can provide any number of standard file handling functions such as open, close, printing, saving, etc.

A) Illustrative User Interface.

Figure 9:
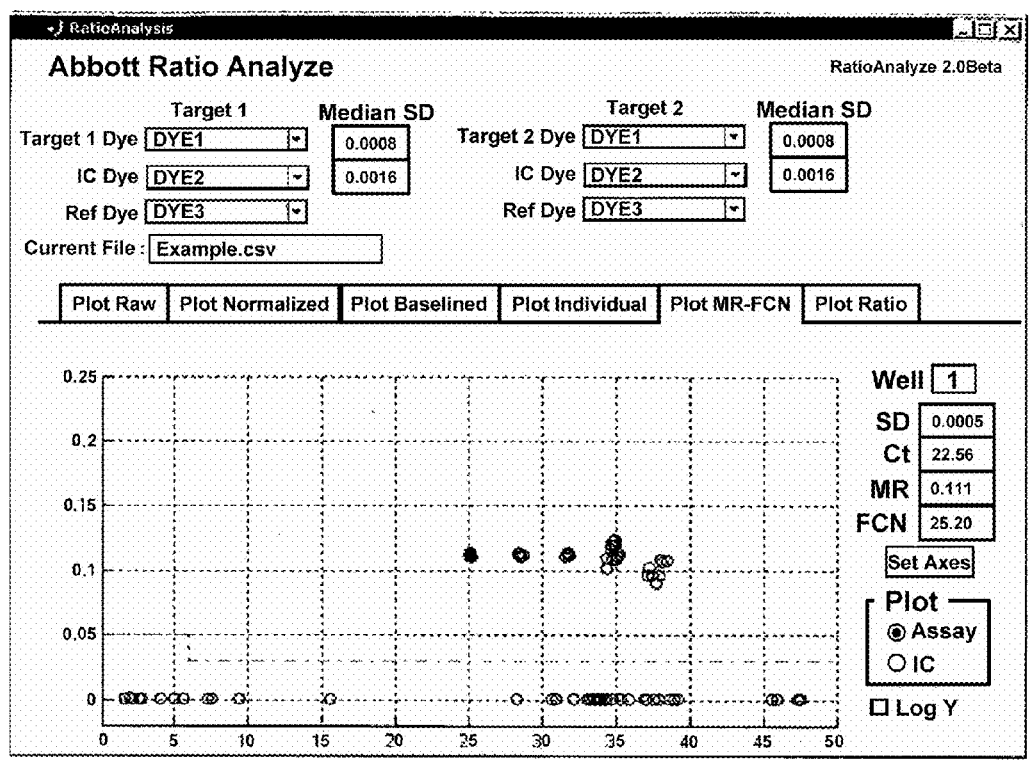
FIG. 9 illustrates an example of a user interface displaying an FCN-MR plot according to embodiments of this invention.
Figure 10:
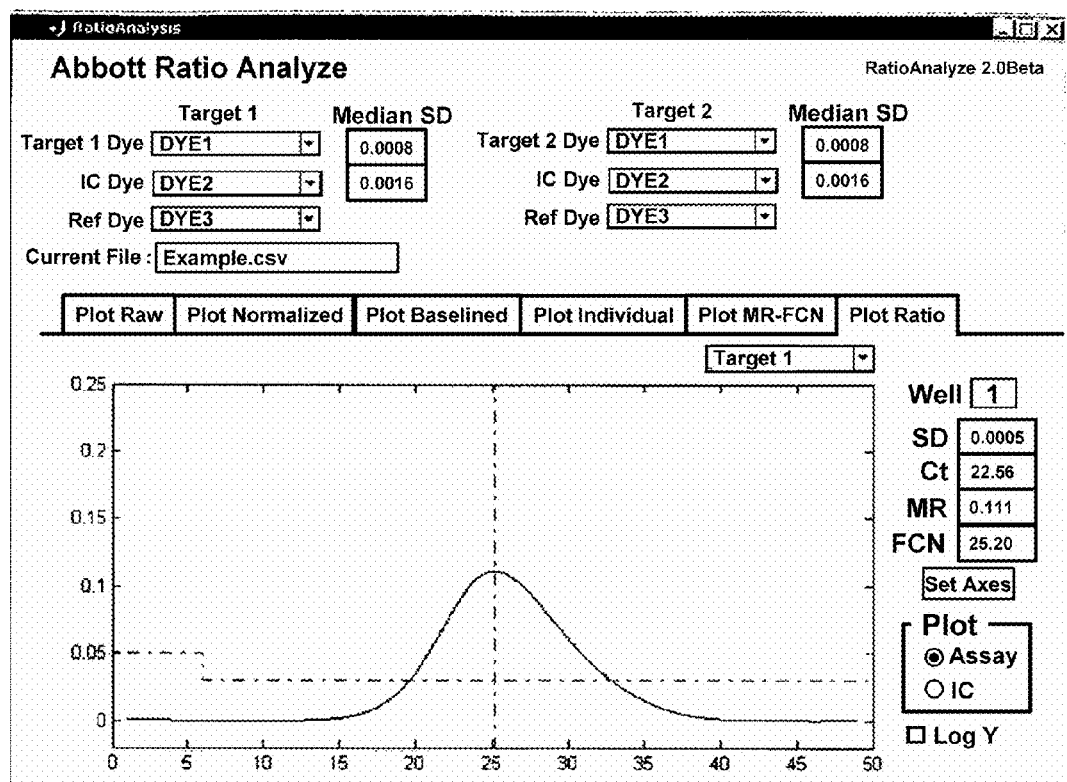
FIG. 10 illustrates an example of a user interface displaying a shifted ratio plot according to embodiments of this invention.

FIG. 9 illustrates a user interface for processing PCR allelic discrimination data according to this invention. In this interface, the selection of appropriate dye(s) corresponding to the various targets (e.g., target 1 (allele 1), target 2 (allele 2), and the like), and optional internal control, and reference responses are selected from popup lists as shown in the window. Tabs for selecting different viewing options (e.g., MR-FCN plot, shifted ratio curve, scatter plot of target signal as a function of target, etc.) are positioned in the middle of the window and are arranged horizontally. FIG. 9 shows that the tab displaying the MR-FCN plot has been selected. FIG. 10 illustrates a user interface showing the same data for well 1, but displaying the shifted ratio curve. Other tabs allow viewing of the raw fluorescence data, normalized fluorescence, baselined data, and the like for all the responses. Drop-down selectors are provided to permit selection of each dye (target). In addition, a tab allows inspection of each response individually. Fields to the right of the plot show calculated response values such as MR, FCN, $C_t$, and standard deviation in the baseline region. Below these calculated values are radio buttons allowing the user to display either the assay data, internal control data, and the like.

B) Embodiment in a Programmed Information Appliance/Device and/or System.

Figure 11:
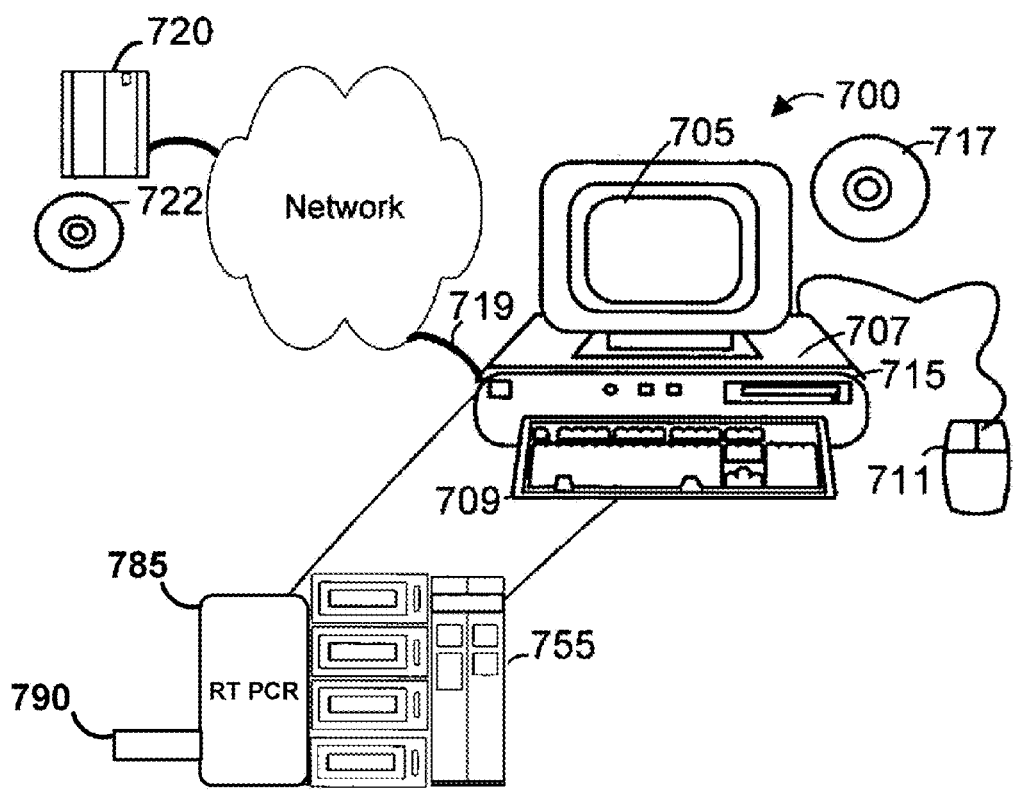
FIG. 11 is a block diagram showing a representative example of a logic device in which various aspects of the present invention may be embodied.

FIG. 11 is a block diagram schematically illustrating one example of a logic device and/or system in which various aspects of the present invention may be embodied. As will be understood from the teachings provided herein, the invention can be implemented in hardware or software or both. In some embodiments, different aspects of the invention can be implemented in either hardware or software and in either client-side logic or server-side logic. Moreover, the invention or components thereof can be embodied in a fixed media (e.g., a computer accessible/computer readable) program component containing logic instructions or data, or both, that when loaded into an appropriately configured computing device can cause that device to perform operations to the invention. In various embodiments a fixed media component containing logic instructions can be delivered to a viewer on a fixed medium for physically loading into a viewer's computer or a fixed medium containing logic instructions can reside on a remote server that a viewer can access through a communication medium in order to download a program component.

As illustrated in FIG. 11, the system comprises an information instrument or digital device 700 that can be used as a logical apparatus for performing logical operations regarding image display or analysis, or both, as described herein. Such a device can be embodied as a general-purpose computer system or workstation running logical instructions to perform according to various embodiments of the present invention. Such a device can also be customized and/or specialized laboratory or scientific hardware that integrates logic processing into a machine for performing various sample handling operations. In general, the logic processing components of a device according to the present invention are able to read instructions from media 717 or network port 719, or both. The central processing unit can optionally be connected to server 720 having fixed media 722. Apparatus 700 can thereafter use those instructions to direct actions or perform analysis as described herein. One type of logical apparatus that can embody the invention is a computer system as illustrated in 700, containing CPU 707, optional input devices 709 and 711, storage media 715, e.g., disk drives, and optional monitor 705. Fixed media 717, or fixed media 722 over port 719, can be used to program such a system and can represent disk-type optical or magnetic media, magnetic tape, solid state dynamic or static memory, etc. The invention can also be embodied in whole or in part as software recorded on this fixed media. Communication port 719 can also be used to initially receive instructions that are used to program such a system and represents any type of communication connection.

FIG. 11 shows that the system can comprise a diagnostic system or an amplification system. Thus, for example the system can include an amplification device such as a thermocycler 785 and optional sample handler 790 for loading and unloading the thermocycler. These additional components can be components of a single system that includes logic analysis and/or control. These devices may also be essentially stand-alone devices that are in digital communication with an information instrument such as 700 via a network, bus, wireless communication, etc., as will be understood in the art. Components of such a system can have any convenient physical configuration and/or appearance and can be combined into a single integrated system. Thus, the individual components shown in FIG. 11 represent just one example system.

C) Embodiment in a Computer-Accessible/Readable Medium.

Figure 12:
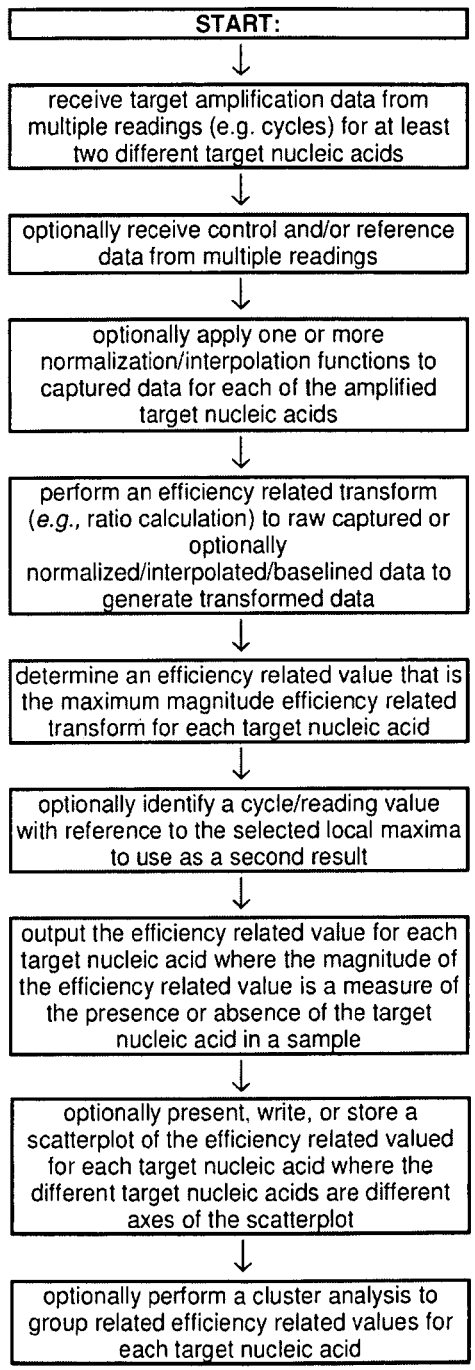
FIG. 12 shows a flowchart for an illustrative embodiment of the methods of this invention.

As indicated above, in certain embodiments, this invention contemplates a computer (machine) accessible/computer (machine) readable medium that provides an instruction set that, if executed by a machine (e.g., a computer processor), will cause the machine to perform the various analytical operations described herein. Thus, in certain embodiments, the machine-readable medium provides instructions that, if executed by a machine, will cause the machine to perform operations comprising: receiving signals from one or more amplification reactions comprising reagents to amplify two or more different target nucleic acids from a single sample where the signals provide data comprising an amplitude measurement representing the degree of amplification of each target nucleic acid in the amplification reaction and the time point in the amplification reaction at which the amplitude is measured, and where the signal provides such data for a multiplicity of time points in the amplification reaction(s); determining an efficiency related transform of said data where said efficiency related transform provides an amplitude measure that is related to the efficiency of amplification in said reaction; determining an efficiency related value for each target nucleic acid that is the maximum magnitude of the efficiency related transform determined for that target nucleic acid; and outputting to a display, printer, or storage medium the efficiency related values and corresponding points in the amplification reaction for each target nucleic acid, where the relative amplitudes of the efficiency related values for each target nucleic acid is an indicator of the presence of each of said nucleic acids in said sample. One illustrative embodiment of such instructions is shown in FIG. 12.

In various embodiments the machine readable medium comprises any tangible medium capable of holding/storing an instruction set. Such media include, but are not limited to a magnetic medium, a flash memory, an optical memory, a DRAM, an SRAM, and the like.

D) Embodiment in Circuitry.

In various embodiments the invention can also be embodied in whole or in part within the circuitry of an application specific integrated circuit (ASIC) or a programmable logic device (PLD). In such a case, the invention can be embodied in a computer understandable descriptor language, which may be used to create an ASIC, or PLD, that operates as described herein.

VII. Other Embodiments

The invention has been described with reference to specific embodiments. Other embodiments will be apparent to those of skill in the art. In particular, a viewer digital information appliance has generally been illustrated as a computer workstation such as a personal computer. However, the digital computing device is meant to be any information appliance suitable for performing the logic methods of the invention, and could include such devices as a digitally enabled laboratory systems or equipment, digitally enabled television, cell phone, personal digital assistant, etc. Modification within the spirit of the invention will be apparent to those skilled in the art. In addition, various different actions can be used to effect interactions with a system according to specific embodiments of the present invention. For example, a voice command may be spoken by an operator, a key may be depressed by an operator, a button on a client-side scientific device may be depressed by an operator, or selection using any pointing device may be effected by the user.

EXAMPLES

The following examples are offered to illustrate, but not to limit the claimed invention.

Example 1

The Applied Biosystems SDS system performs allelic discrimination using an end-point assay system which attempts to determine the "amount" of amplification by measuring the amount of fluorescence generated which should relate to whether that allele is present. Total fluorescence generated in a PCR reaction is not necessarily well related to efficiency of amplification. A higher concentration but less efficient amplification can generate more fluorescence than a higher efficiency but lower concentration amplification In addition, final fluorescence is generally determined after the PCR reaction has gone beyond the exponential amplification region where other aspects of the reaction can significantly affect performance. For this reason, final fluorescence levels are variable indicators of amplification. In addition in order to get adequate fluorescence measurements, the SDS system makes a series of pre and post PCR fluorescence reads which increases the processing time.

MaxRatio generated MR values are determined in the early cycles as the amplification rises above the background Because these MR values are determined while the reaction is still near exponential, they are more directly related to amplification efficiency and should be more useful for determining AD or SNP calls than total fluorescence MaxRatio analysis uses most of the measurements from a real-time PCR reaction. For this reason, there is the ability to make measurements of the quality and validity of the PCR amplification not available in the total fluorescence method. In addition, using MR values would only require the PCR cycling protocol and would eliminate the need the pre and post reads significantly reducing processing time.

Assay runs from DVT SNP reactions were utilized to test the methods described herein. The deep vein thromobosis prototype assay consisted of identification of SNPs (Single Nucleotide Polymorphisms) within 3 genes: Factor V (G1691A) ("Factor V Leiden"), Factor II (G20210A) and MTHFR (C677T). The Factor V Leiden mutation is the most common genetic risk for venous thrombosis and pulmonary embolism, present in 5% of the Caucasian population and in 20-40% of individuals with a history of venous thromboembolism. Factor V Leiden heterozygotes are at a 7-fold increased risk for venous thromboembolism. The Factor V Leiden mutation is responsible for 85-95% of APC resistance. APC is a neutral anticoagulant that inactivates factors Va and VIIIa. The Factor II (Prothrombin) mutation is associated with elevated circulating levels of prothrombin. Greater availability of prothrombin is believed to lead to greater conversion to thrombin and an increased chance of thrombosis. The MTHFR (methylene tetrahydrofolate reductase) C677T mutation is tentatively associated with increased risk of venous thrombosis.

Figure 2A:
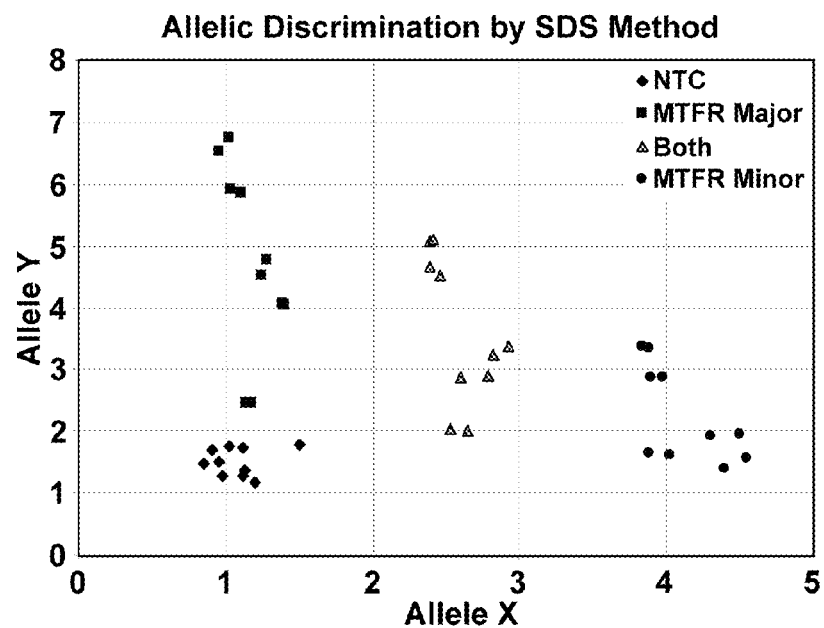
FIGS. 2A and 2B show the results of a real time PCR allelic discrimination analysis using a conventional Ct analysis (FIG. 2A) and a MaxRatio analysis (FIG. 2B).
Figure 2B:
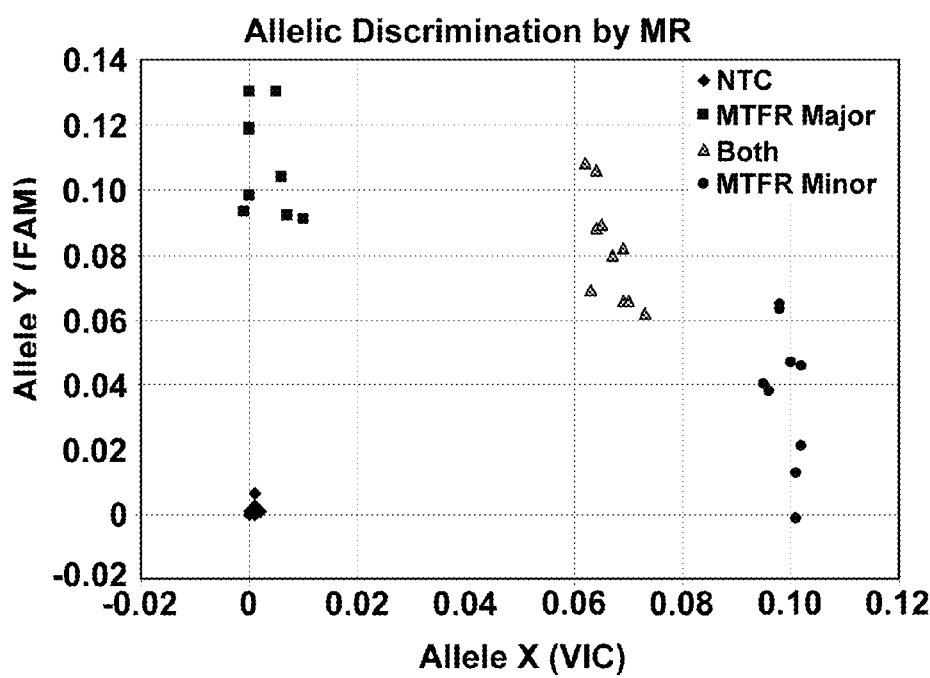

These files were processed in SDS for the allelic discrimination results. Because these are known samples, calls were predetermined. An SDS results report was generated. Component fluorescence files were exported from SDS and run in MultiAnalyze 3.0 to generate MR values. SDS generated total fluorescence values and MR values were imported into Excel for plot generation. Results are shown in FIGS. 2A and 2B. FIG. 2A shows the results generated by SDS. FIG. 2B shows the results generated using MaxRatio.

The MTHFR Major cluster is much more clearly separated from the no template control (NTC) using MR values. In general, clusters are at least as well separated using the MR method as with SDS.

Figure 3:
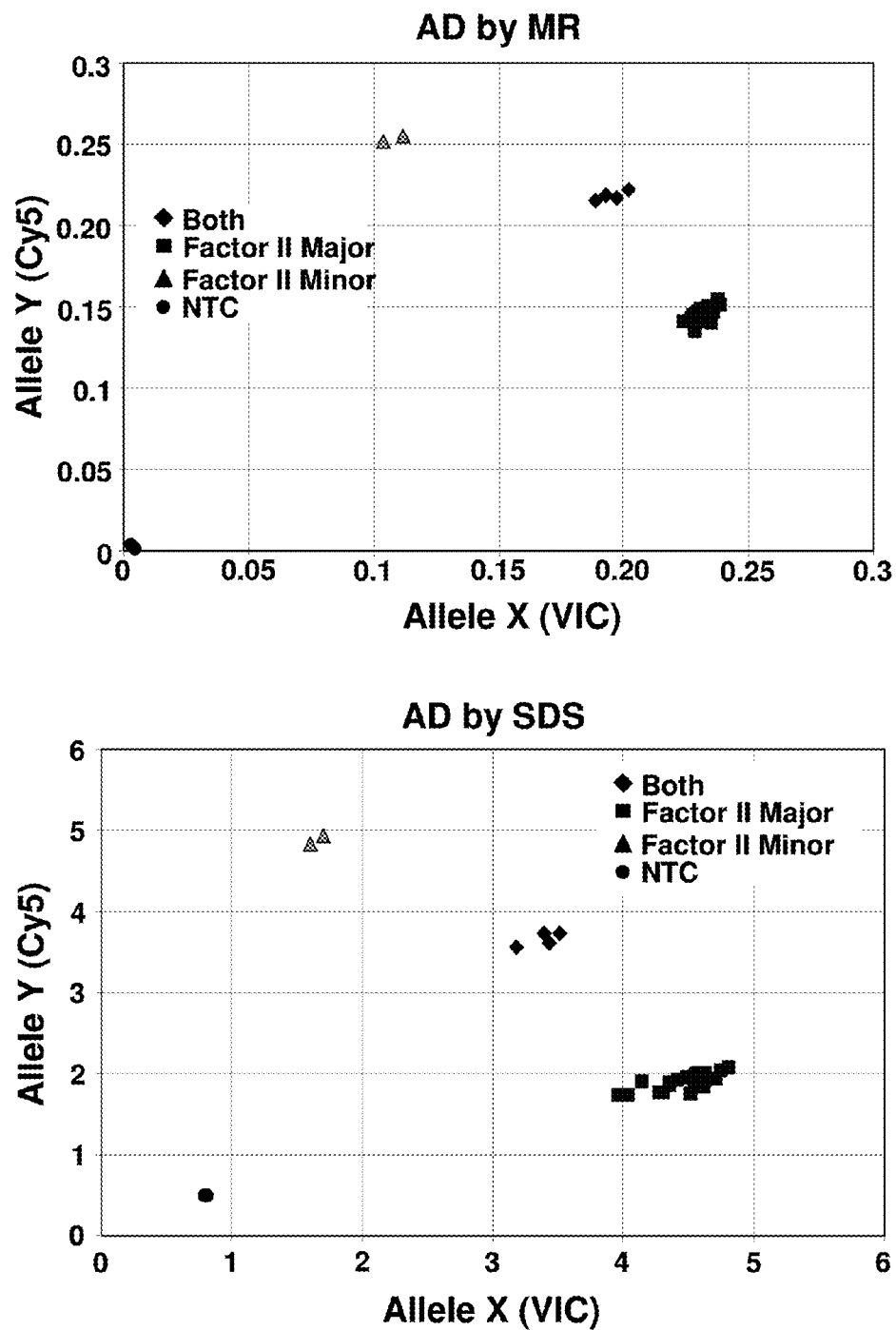
FIG. 3 shows the results of a real time PCR allelic discrimination analysis using a conventional Ct analysis (upper panels) and a MaxRatio analysis (lower panels).

A second set of comparisons is provided in FIG. 3. MaxRatio clearly reduces the variability and provides a cleaner signal (tighter clustering) which facilitates discrimination of the alleles. It is noted that the assay conditions were optimized for SDS and not for a maxratio analysis. It is believed that optimization of assays for maxratio can provide even cleaner results.

It is understood that the examples and embodiments described herein are for illustrative purposes and that various modifications or changes in light thereof will be suggested by the teachings herein to persons skilled in the art and are to be included within the spirit and purview of this application and scope of the claims. All publications, patents, and patent applications cited herein or filed with this application, including any references filed as part of an Information Disclosure Statement, are incorporated by reference in their entirety It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of discriminating two or more different alleles, said method comprising:
    performing one or more amplification reactions comprising reagents to amplify two or more different alleles from a single sample;
    collecting data comprising sequential amplification signal measurements representing the degree of amplification of each allele in the amplification reaction, and the time point in the amplification reaction at which the amplification signal is measured, for a multiplicity of time points in the amplification reaction(s);
    determining an efficiency related transform of said data where said efficiency related transform provides an amplitude measure that is related to the efficiency of amplification in said reaction;
    determining an efficiency related value for each allele that is the maximum magnitude of the efficiency related transform determined for that allele; and
    outputting to a display, printer, or storage medium the efficiency related values for each allele, where the relative amplitudes of the efficiency related values for each allele is an indicator of the presence of each of said allele in said sample.

2. The method of claim 1, wherein said reagents to amplify two or more alleles are in a single amplification reaction.

3. The method of claim 1, wherein said reagents to amplify two or more alleles are distributed so that each amplification reaction comprises reagents to amplify different alleles.

4. The method of claim 1, wherein said reagents to amplify two or more alleles are distributed so that each amplification reaction comprises reagents to amplify a different alleles.

5. The method of claim 1, wherein said collecting comprises real-time monitoring of a PCR reaction.

6. The method of claim 1, wherein the time points in the amplification reaction are measured in cycle number.

7. The method of claim 1, wherein the points in the amplification reaction are measured in reaction time.

8. The method of claim 1, wherein said amplifying comprises amplifying at least three different alleles.

9. The method of claim 1, wherein said amplifying comprises amplifying at least five different alleles.

10. The method of claim 1, wherein said alleles comprise a first nucleic acid derived from a first allele of a gene and a second nucleic acid derived from a second allele of said gene.

11. The method of claim 10, wherein outputting comprises outputting information indicating whether said sample is homozygous for said first allele, homozygous for said second allele or heterozygous for both alleles.

12. The method of claim 1, wherein the efficiency related transform is selected from the group consisting of the ratio transform of the signal measurements, the shifted ratio transform of the signal measurements, the first derivative of the signal measurements, the differences between sequential signal measurements, and the slope or gradient of the log of the signal measurements.

13. The method of claim 1, wherein the efficiency related transform (ERT) is calculated as:

$$ERT = (Signal_{n+1}/Signal_n) - 1 \text{ or} \qquad (a)$$

$$ERT = (Signal_n/Signal_{n-1}) - 1 \qquad (b)$$

where $Signal_n$ is the signal produced at cycle number n, $Signal_{n+1}$ is the signal produced at the subsequent cycle number, Signaln−1 is the signal produced at the previous cycle number, and n ranges from 1 up to the number of amplification cycles analyzed in the reaction for formula (a) and n ranges from 2 up to the number of amplification cycles−1 analyzed in the reaction for formula (b).

14. The method of claim 1, wherein the efficiency related value is the maximum gradient of the log of the signal measurements.

15. The method of claim 1, wherein the efficiency related value is the maximum ratio of the signal measurements.

16. The method of claim 1, wherein the efficiency related value is the maximum first derivative of the signal measurements.

17. The method of claim 1, wherein additional signal values are generated by interpolating points between the signal measurements.

18. The method of claim 17, wherein said additional signal values are generated by interpolating points between the signal measurements using cubic splines.

19. The method of claim 1, wherein said efficiency related transform additionally provides a measure of the time or cycle number in said amplification reaction(s).

20. The method of claim 19, wherein said method further comprises calculating a reaction point that is the fractional cycle number or time at which the maximum magnitude of the efficiency related transform occurs.

21. The method of claim 19, wherein said method further comprises calculating an adjusted reaction point.

22. The method of claim 21, wherein the adjusted reaction point is equal to the reaction point minus the log base 2 of the efficiency related value.

23. The method of claim 21, wherein the adjusted reaction point is equal to the reaction point minus the log base 2 of the signal intensity above background.

24. The method of claim 1, wherein:
    said determining an efficiency related value for each allele that is the maximum magnitude comprises identifying a peak in the efficiency related transform as a function of time or cycle number.

25. The method of claim 24, wherein said method further comprises:
    determining the width of said peak;
    comparing the width of the peak to a selected range of acceptable peak widths; and
    outputting to a display, printer, or storage medium an indicator identifying the nucleic acid amplification reaction as possibly abnormal if the peak width determined is greater than or less than a selected range of acceptable peak widths.

26. The method of claim 25, wherein the peak width is calculated using only efficiency related transforms that occur at or before the reaction point value of the efficiency related value.

27. The method of claim 1, wherein amplification reaction is performed with a set of probes that comprises a FRET probe that is complementary to all or a portion of one of the amplified alleles.

28. The method of claim 1, wherein amplification reaction is performed with a set of probes that comprise a molecular beacon that is complementary to all or a portion of one of the amplified alleles.

29. The method of claim 1, wherein the alleles comprise single nucleotide polymorphisms.

* * * * *